(12) United States Patent
Huang et al.

(10) Patent No.: US 10,070,784 B2
(45) Date of Patent: Sep. 11, 2018

(54) OCT VITRECTOMY PROBE

(71) Applicants: Oregon Health & Science University, Portland, OR (US); James Fujimoto, Cambridge, MA (US); Chen Lu, Cambell, CA (US); David Huang, Portland, OR (US); Yimin Wang, Portland, OR (US); David Wilson, Portland, OR (US); J. Timothy Stout, Portland, OR (US)

(72) Inventors: David Huang, Portland, OR (US); Yimin Wang, Portland, OR (US); David Wilson, Portland, OR (US); J. Timothy Stout, Houston, TX (US); James Fujimoto, Cambridge, MA (US); Chen Lu, Cambridge, MA (US)

(73) Assignee: Oregon Health & Science University, Portland, OR (US)

(*) Notice: Subject to any disclaimer, the term of this patent is extended or adjusted under 35 U.S.C. 154(b) by 0 days.

(21) Appl. No.: 14/890,035

(22) PCT Filed: May 12, 2014

(86) PCT No.: PCT/US2014/037718
§ 371 (c)(1),
(2) Date: Nov. 9, 2015

(87) PCT Pub. No.: WO2014/183123
PCT Pub. Date: Nov. 13, 2014

(65) Prior Publication Data
US 2016/0089025 A1    Mar. 31, 2016

Related U.S. Application Data

(60) Provisional application No. 61/822,176, filed on May 10, 2013.

(51) Int. Cl.
*A61B 3/12* (2006.01)
*A61B 3/10* (2006.01)
(Continued)

(52) U.S. Cl.
CPC ............ *A61B 3/12* (2013.01); *A61B 3/102* (2013.01); *A61B 5/0066* (2013.01);
(Continued)

(58) Field of Classification Search
CPC ......... A61B 3/12; A61B 3/102; A61B 5/0066; A61B 5/0261; A61F 9/00736; G02B 3/0087; G02B 26/005; G02B 26/0833; G02B 27/141; G02B 27/30; G01B 9/02063; G01B 9/02004; G01B 9/02091; G01B 2290/65
(Continued)

(56) References Cited

U.S. PATENT DOCUMENTS

| | | | |
|---|---|---|---|
| 8,254,023 B2* | 8/2012 | Watson | G02B 21/002 359/368 |
| 2007/0081166 A1* | 4/2007 | Brown | A61B 3/1005 356/479 |

(Continued)

*Primary Examiner* — Jie Lei
(74) *Attorney, Agent, or Firm* — Schwabe, Williamson & Wyatt, P.C.

(57) ABSTRACT

Disclosed herein are vitrectomy probes configured for use with optical coherence tomography.

9 Claims, 10 Drawing Sheets

(51) Int. Cl.
- *G02B 3/00* (2006.01)
- *G01B 9/02* (2006.01)
- *A61B 5/00* (2006.01)
- *A61F 9/007* (2006.01)
- *A61B 5/026* (2006.01)
- *G02B 26/00* (2006.01)
- *G02B 26/08* (2006.01)
- *G02B 27/14* (2006.01)
- *G02B 27/30* (2006.01)

(52) U.S. Cl.
CPC ........ *A61B 5/0261* (2013.01); *A61F 9/00736* (2013.01); *G01B 9/02004* (2013.01); *G01B 9/02063* (2013.01); *G01B 9/02091* (2013.01); *G02B 3/0087* (2013.01); *G01B 2290/65* (2013.01); *G02B 26/005* (2013.01); *G02B 26/0833* (2013.01); *G02B 27/141* (2013.01); *G02B 27/30* (2013.01)

(58) Field of Classification Search
USPC ....... 351/221, 205, 206, 208, 210, 212, 216, 351/236, 246; 356/477, 479, 497, 498; 600/425
See application file for complete search history.

(56) References Cited

U.S. PATENT DOCUMENTS

| | | | |
|---|---|---|---|
| 2009/0021724 A1* | 1/2009 | Mahadevan-Jansen | A61B 5/0066 356/73 |
| 2009/0284749 A1* | 11/2009 | Johnson | A61B 5/0066 356/497 |
| 2014/0300866 A1* | 10/2014 | Fukuma | A61B 3/0058 351/208 |
| 2014/0327947 A1* | 11/2014 | Lin | G02B 26/103 359/210.1 |

* cited by examiner

OCT VITRECTOMY PROBE

PRIORITY CLAIM

The application claims the benefit of U.S. Provisional Application No. 61/822,176, filed May 10, 2013, which is incorporated by reference herein in its entirety.

FIELD

Generally, the field is optical probes for use in surgery. More specifically, the field is an optical probe that uses optical coherence tomography.

BACKGROUND

Optical coherence tomography (OCT) is a high-resolution cross-sectional imaging tool that has become important in diagnosing ocular and other medical diseases (Huang D et al, Science 254, 1178-1181 (1991); incorporated by reference herein.) In OCT, the depths of sample reflections are measured indirectly by interference with a reference reflection. OCT provides both high detection sensitivity (photon shot-noise limited) and high resolution (better than 10 µm). It is often implemented with fiber optics for ease of alignment, compactness, modularity, and stability. The imaging speed of OCT has been improved greatly with the development of the Fourier domain (FD) technique (Wojtkowski R et al, J Biomed Opt 7, 457-463 (2002): de Boer J F Opt Lett 28, 2067-2069 (2003); and Choma M A et al, Opt Express 11, 2183-2189 (2003); all of which are incorporated by reference herein) making it possible to use OCT for clinical applications.

Catheter-based imaging has extended the use of OCT to blood vessels (Fujimoto J G et al, Heart 82, 128-133 (1999) and Yang X D et al, Opt Express 11, 2416-2424 (2003); gastrointestinal tracts (Rollins A M et al, Opt Lett 24, 1358-1360 (1999) Izatt J A et al, IEEE J Selected Topics Quantum Electron 2, 1017-1028 (1996); both of which are incorporated by reference herein) respiratory tracts (Pitris C et al, Am J Respir Crit Care Med 157, 1640-1644 (1998), incorporated by reference herein), and genitouninary tracts (Yaqoob Z et al, J Biomedical Optics 11, 063001-1-19 (2006); incorporated by reference herein.) OCT has proved useful in guiding some important endoscopic procedures, such as fine needle aspiration and endoscopic mucosal resection. OCT angioscopy has higher resolution than X-ray and ultrasound and can detect atherosclerotic plaques vulnerable to rupture. Miniature side-scanning OCT catheters have been successfully used for coronary angioscopy (Schmitt J et al, European Cardiology May, 2005).

SUMMARY

Disclosed herein is an optical probe system for OCT tissue structure imaging. A MEMs mirror will be used to deflect probe beam in two dimensions. A graded-index or gradient-index (GRIN) lens will relay the probe beam onto biological sample to supply forward beam steering. An electrowetting lens (EWL) will be used for automated focus adjustment. This probe can also work in side scanning mode with a micro prism attached at the distal end of the GRIN lens. This design will have a small caliber to minimize tissue disruption. Two dimensional scanning can be achieved.

DETAILED DESCRIPTION

Figure 1:
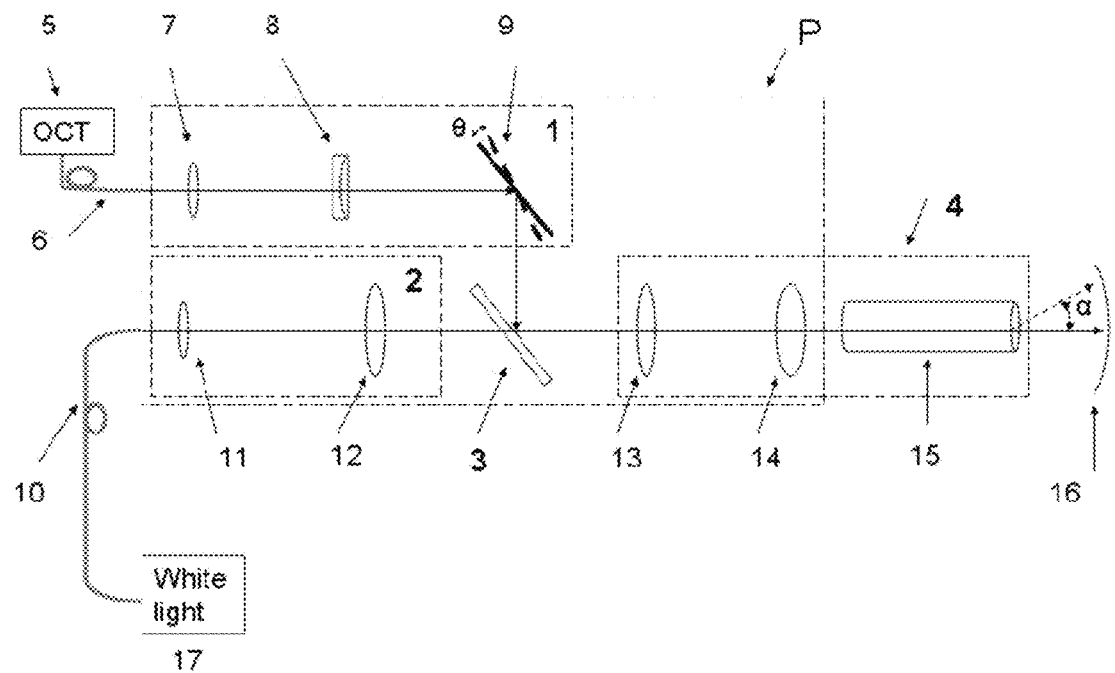
FIG. 1. Diagram of vitrectomy probe with MEMs mirror as optical beam deflector.

The practical employment of OCT probes in surgeries of solid organs or internal cavities has been limited by the lack of a miniature forward-scanning probe. So far, forward scanning OCT probes have been bulky and complex. Clearly, miniaturized probes that use high speed, high sensitivity, and high resolution FD-OCT technology, this probe are needed to make many parts of the human body accessible to OCT-guided procedures.

OCT probes are capable of delivering, focusing and scanning light inside organs and collecting backscattered light from the tissue. Generally, such probes comprise an optical coupling element at the proximal end and optical focusing and beam-directing elements at the distal end. Most currently available OCT probes are designed for side imaging, wherein circular sectional images of the organ walls are obtained by rotating a fiber or a micromotor. Such a configuration is appropriate for angioscopy or endoscopy, in which the shape of the anatomical structure (blood vessel, gut, trachea, bronchus or other tube-like anatomical structure) guides insertion, and simultaneous fiber-optic visualization or x-ray fluoroscopy can guide further probe placement.

A forward imaging probe is used in situations where the OCT image itself is used to guide the advance and positioning of the probe in a solid anatomical structure (i.e. brain, breast) or where the target to be imaged is ahead of the probe rather than on the side (i.e. vitreous cavity, bladder). When an OCT probe is used in intraocular imaging, forward imaging ability is preferable to detect retina layer structures and avoid touching retina vessels. OCT cannot be applied to the operating room because currently available OCT systems require the patient to be in a sitting position which is incompatible with surgery. Forward-imaging probes require the location of the beam scanning actuators near the probe tips. The size of the actuators limits the extent of probe miniaturization. The development of a smaller diameter (<1 mm) forward-imaging OCT probe with a wide field of view is highly desired in probe-guided procedures, such as vitreoretinal imaging, deep brain electrode insertion, spinal and subdural anesthesia catheter insertion, and needle biopsies.

Micro-Electro-Mechanical System

A Micro-Electro-Mechanical System (MEMs) is a technology to miniaturize mechanical and electro-mechanical elements at the scale of micrometers to millimeters using the technique of microfabrication (Bustjilo J M et al, Proceedings of the IEEE 86, 1552-1573 (1998) and Kovacs G T A et al, Proceedings of the IEEE 86, 1536-1551 (1998); both of which are incorporated by reference herein. A number of microactuators including optical switches and mirrors for image display, wavefront shaping and light beam steering are known in the art.

A MEMs scanning mirror is a silicon device with a mirror located at about the center. This mirror is connected to small flexures allowing it to oscillate. The 2D MEMs scanner oscillates vertically and horizontally to redirect or modulate a light beam. More recently, MEMS technology has shown great potential in biomedical engineering especially for endoscopic imaging. The use of a MEMs mirror is proposed to facilitate endoscopic beam steering because of the system's small size and excellent microbeam manipulating capacity.

Electrowetting Lens

Many optical systems have adjustable focus and magnification. Miniaturized systems may have adjustable focus and magnification using systems that do not rely on mechanical motion. Such systems include processes that involve injecting fluids such as water or oil in a deformable transparent chamber with external pump. In some examples, the meniscus between water and oil can be used as an optical lens and with a focal length is adjusted through changing the curvature of this meniscus (Dong L et al, Nature 442, 551-554 (2006) and Berge B and Peseux J, Euro Phys J E 3, 159-163 (2000); both of which are incorporated by reference herein. Electro-optic materials have also been used to construct a variable power lens in a thin film, for opto-electronic applications (Yamada M et al, Appl Phys Lett 69, 3659 (1996); incorporated by reference herein.)

Piezoelectric-Transducer Actuator

Piezoelectric transducer (PZT) actuators have been widely used in mechanical actuation (chee C Y K et al, J Intell Mater Sys Struct 9, 3-19 (1998); incorporated by reference herein. A PZT can undergo mechanical strain when subjected to an applied electric field. Because of high piezoelectric constant, a large deflection at PZT actuator's tip can be easily achieved with small cantilever size. The small cantilever size can provide high resonant frequency for high speed operation. (Kim Y S et al, Sensors and Actuators A: Physical 103, 122-129 (2003); incorporated by reference herein). A PZT actuator has the advantage of low power consumption due to small operation voltage and leakage current. It can provide accurate movement with compact size for different applications which require precise position control.

Referring to FIG. 1, the vitrectomy probe P comprises beam steering system 1, fundus illumination system 2, and beam delivery system 4. Mirror 3 is a dichroic mirror which is employed to reflect the probe beam from beam steering system 1, while transmitting white illumination light from illumination system 2.

Beam Steering System

Referring to FIG. 1, the beam steering system 1 comprises a collimating lens 7, EWL 8 and MEMs mirror 9. The beam steering system is configured so that a light beam from sample arm fiber 6 of an OCT system 5 is collimated by lens 7, passing through EWL 8 and reflected by MEMs mirror 9. The reflected light will be reflected again by dichroic mirror 3 and entering into beam delivering system 4.

Fundus Illumination System

Referring to FIG. 1, the fundus illumination system 2 preferably comprises a collimating lens 11 and lenses 12. Multimode fiber 10 is connected with white light source 17, such as a Xenon arc lamp. White illumination light from multimode fiber 10 will be collimated by lens 11, passing through lens 12 and dichroic mirror 3, and entering beam delivering system 4.

Beam Delivering System

Referring to FIG. 1, beam delivering system 4 comprises two lenses 13, 14, and a GRIN lens 15. GRIN lens has a diameter of 0.5 mm and length of 4 pitches (~20 mm). Lenses 13 and 14 will relay the surface of MEMs mirror 9 onto the entrance of GRIN lens 15. Preferably, the GRIN lens 15 will couple OCT probe beam into human eye and collect the reflected light. The white light from illumination system 2 will pass through GRIN lens 15 and illuminate retina 16 at an extended angle. The overall diameter of the probe needle shaft may be less than 0.81 mm (20 gauge), small enough to fit through scleral incisions made for vitreoretinal surgery.

OCT Setup

Figure 2:
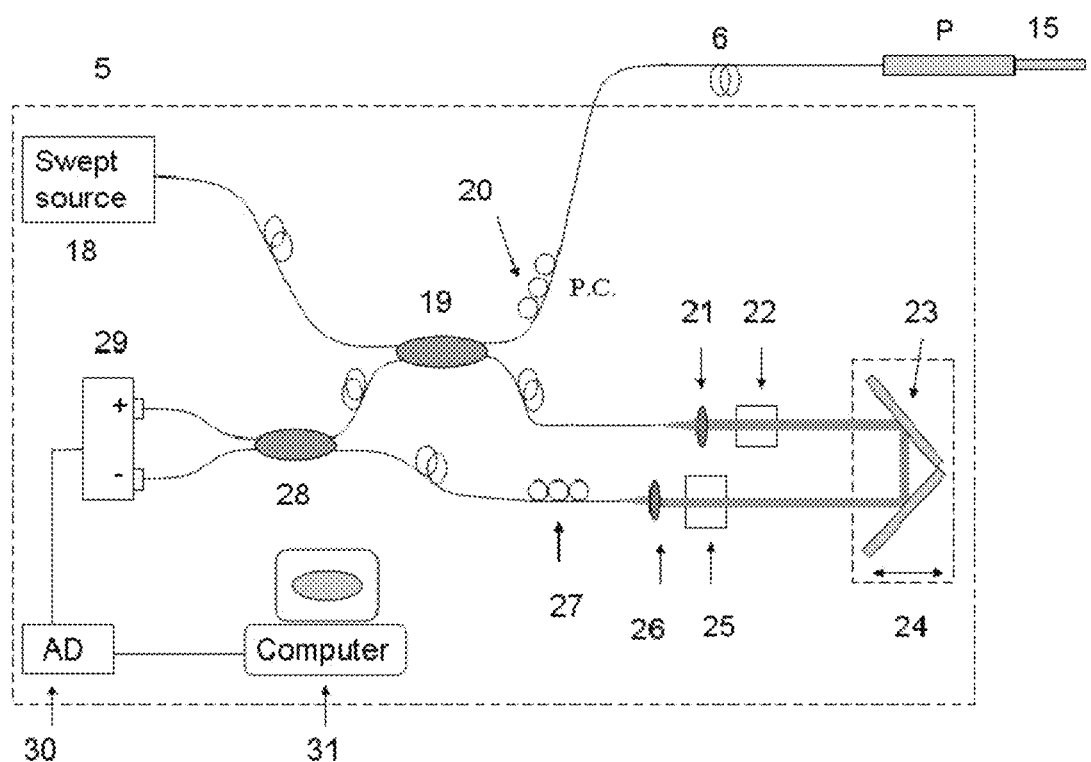
FIG. 2. Diagram of Swept source OCT setup.

A high speed SS-OCT system 5 will be employed. Referring to FIG. 2, the swept source OCT system preferable comprises a tunable laser 18. Its wavelength is 1050 nm with 100 nm tuning range. The tuning cycle of the laser has a repetition rate of 100 kHz and a duty cycle of 50%. Light from swept source 18 is coupled into a two by two fiber coupler 19 through single mode optical fiber. One portion of light proceeds to the sample arm, and the other portion to the reference arm.

In the sample arm, a polarization control unit 20 is used to adjust light polarization state. The exit light from fiber coupler 19 is coupled into vitrectomy probe P through single mode optical fiber 6. The average light power onto human retina is 1.9 mW, which is consistent with safe ocular exposure limit set by the American National Standard Institute (ANSI). The reference arm preferably comprises a collimating lens 21, water cell 22, retro-reflector 23, glass plate 25 and collimating lens 26. Glass plate 25 is used to balance the dispersion between OCT sample and reference arms. Water cell 22 is used to compensate the influence of dispersion in human eye. Retro-reflector 23 is mounted on a translation stage 24 which can be moved to adjust the path length in the reference arm.

Light from sample and reference arm interfere at beam splitter 28. A polarization control unit 27 is used to adjust the beam polarization state in the reference arm to maximum the interference signal. The optical interference signal from beam splitter 28 is detected by a balanced detector 29, sampled by an analog digital conversion unit 30 and transferred into computer 31.

PZT Actuator Steering System

Figure 3:
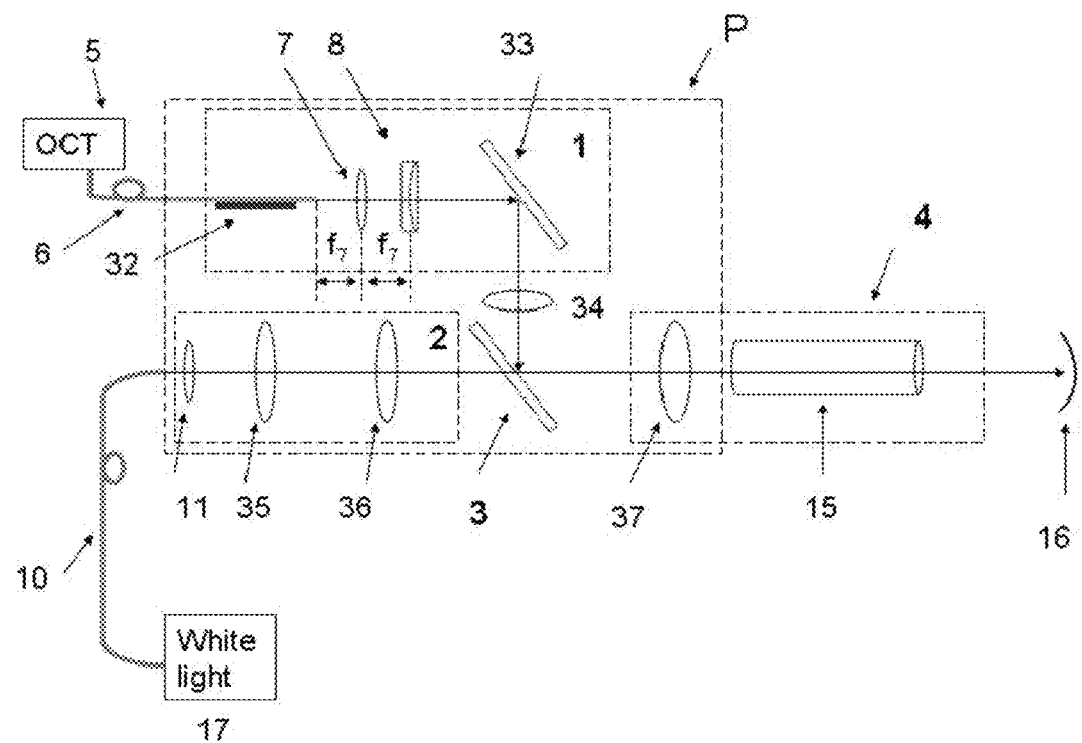
FIG. 3. Diagram of vitrectomy probe with PZT actuator as optical beam deflector.

Beam steering devices other than a MEMs mirror may be used depending on the intended application. One example of such a device is a PZT actuator. Referring to FIG. 3, beam steering system 1 includes a PZT actuator 32, a collimating lens 7, an EWL 8 and mirror 33. EWL 8 is positioned at the back focal plane of lens 7.

Figure 4:
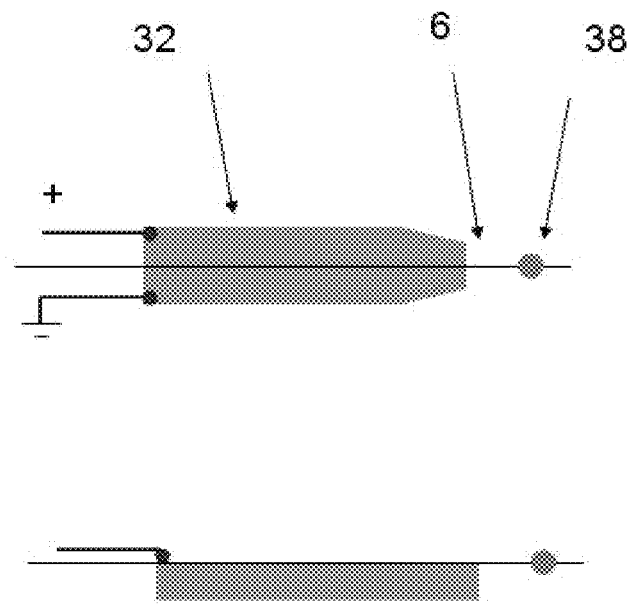
FIG. 4. Diagram of single mode fiber fixed onto PZT bender.

Referring to FIG. 4, the PZT actuator 32 is a tapered PZT bender. UV curved epoxy is used to fix the single mode fiber 6 on the PZT bender. A drop of epoxy 38 can be fixed on the fiber tip to reduce the resonant frequency of the fiber cantilever. Optical fiber 6 is angle cleaved at its tip to reduce back reflection.

Referring to FIG. 3, the fundus illumination system 2 comprises lens 11, 35 and 36. Multimode fiber 10 is connected with white light source 17. White light from fiber 10 will be collimated by lens 11, passing through lens 35, 36 and dichroic mirror 3, and entering beam delivering system 4.

Referring to FIG. 3, beam delivering system 4 comprises a lens 37 and GRIN lens 15. Lenses 34 and 37 relay the position of EWL lens 8 onto the entrance surface of the GRIN lens 15. The GRIN lens 15 will couple OCT probe beam into human eye and collect the reflected light. White light from illumination system 2 will pass through RGIN lens 15 and illuminate retina 16 with an extended angle.

Side Scanning System

Figure 5:
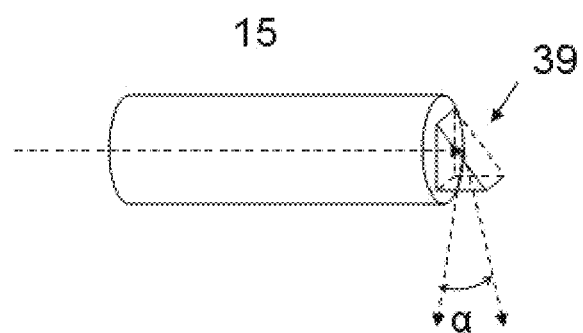
FIG. 5. Diagram of side scanning probe with micro-prism on the output surface of GRIN lens.

The disclosed probe can also be used as a side scanning system. Referring to FIG. 5, a right angle prism 39 is attached to the output surface of GRIN lens 15. The forward transmitting beam from GRIN lens 15 will be folded 90 degrees to sideways by the prism 39. Therefore, two dimensional side-scanning can be achieved to detect tissue structure surrounding the probe.

EXAMPLES

The following examples are illustrative of disclosed methods. In light of this disclosure, those of skill in the art will recognize that variations of these examples and other examples of the disclosed method would be possible without undue experimentation.

Example 1

Described herein is one example of a use of the disclosed probe to image biological tissue with forward beam scanning. Referring to FIG. 1 a sampling beam from a swept source OCT system 5 is coupled into the probe P through optical fiber 6 and collimated by lens 7. The collimated beam transmits through EWL lens 8 and deflected by MEMs mirror 9. After the beam is reflected by dichroic mirror 3, the it transmits through lens 13 and 14, and enters GRINs lens 15. In this design, the MEMs mirror 9 is relayed to the entrance of GRIN lens 15. Therefore, during MEMs mirror oscillation for beam steering, the light beam position on the GRIN lens entrance surface has a minimum variation. Output light from the GRINs lens is focused into the retina 16.

For the MEMs mirror, the deflection angle of the reflected beam is two times the mechanical rotation angle $\theta$ (FIG. 1) of the mirror surface. If the ratio of the focal length between lens 13 and 14 is m, the deflection angle $\alpha$ of probe beam will be $\alpha = 2m\theta$.

Figure 6:
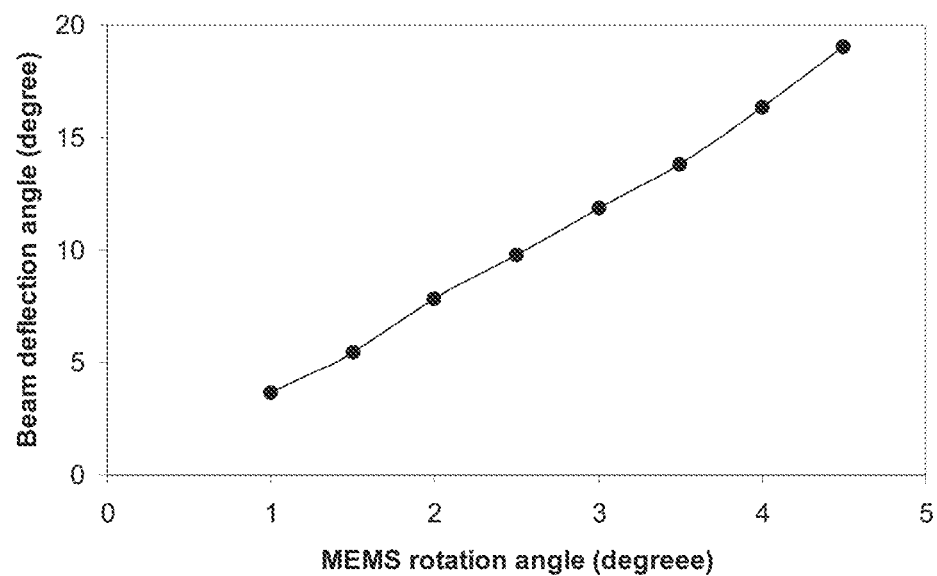
FIG. 6. Relationship between the probe beam deflection angle and the rotation angle of MEMs mirror.

FIG. 6 shows the deflection angle of the probe beam at different MEMs mirror rotation angles, simulated with ZEMAX software. The maximum beam deflection angle is $\alpha > \pm 180$. In this simulation, the ratio of the focal length between lens 13 and 14 is 2. Therefore, the angle magnification factor is 4. For 2D MEMs mirror, the two mirror axis is independently controlled to address beam deflection over two dimensions.

Example 2 Auto Focusing

Focal length of EWL lens 8 can be controlled electrically through changing the curvature of the interface between two aqueous materials inside the lens. This will lead to the variation of the working distance between the distal end of the GRIN lens and human retina.

Figure 7:
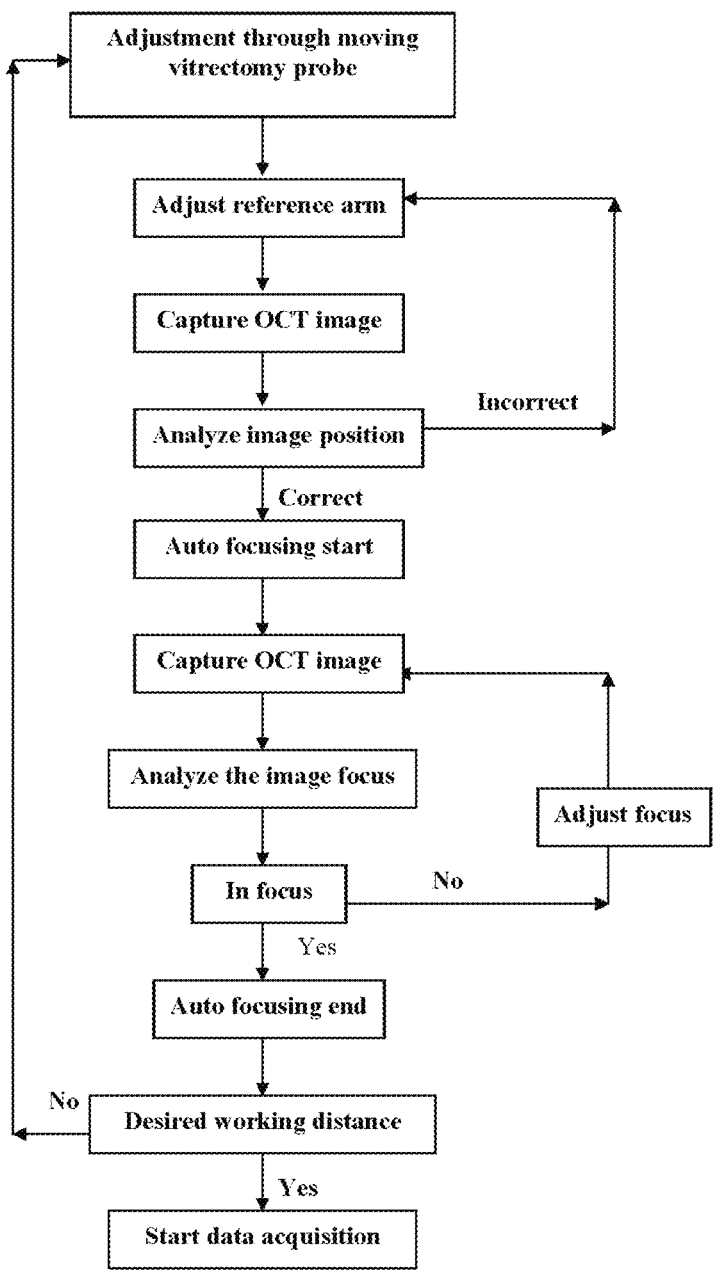
FIG. 7. Flow chart of auto focusing.

A working mechanism of auto focusing is shown in the flow chart in FIG. 7. If the operator moves the probe back and forth, the distance between GRIN lens and the retina can be changed. This will lead to the variation of the retina position in the depth dimension of the OCT image. Retina position change in the OCT image can be compensated through changing the path length of the OCT reference arm by translational motion of the stage 24 as shown in FIG. 2. Stage 24 is adjusted repeatedly until the retinal position is in the desired region in the captured OCT image. After that, auto focusing will start. At each focal length of EWL 8, the OCT image will be captured and analyzed. If the retina is not in focus, focal length of EWL 8 will be changed again. This process will be repeated multiple times until human retina is in focus and the captured image quality is the best. Then focal length of EWL 8 will be set and auto focusing process ends. If the vitrectomy probe is at the desired working distance, then OCT data acquisition will begin. If not, vitrectomy probe will be moved again and auto focusing process will be repeated.

Figure 8:
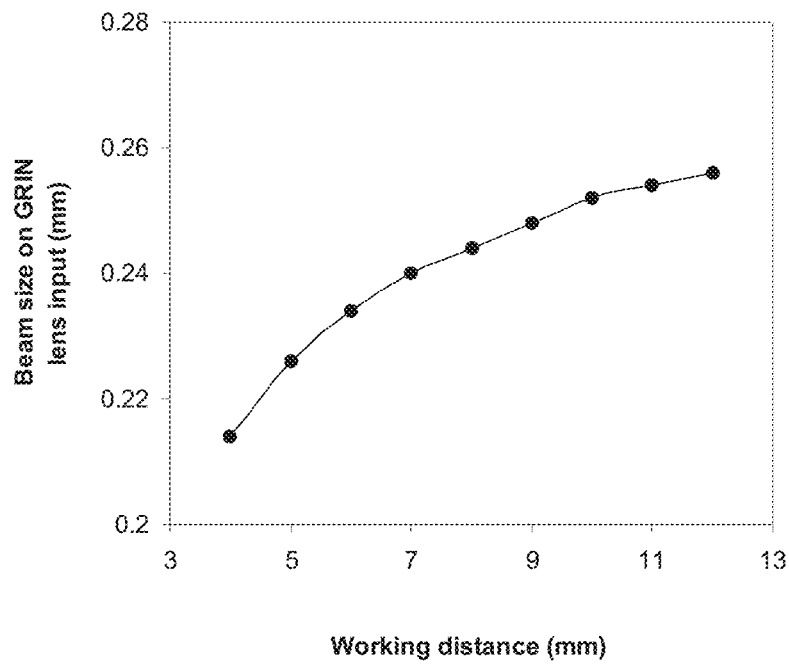
FIG. 8. Relationship between probe beam size on the entrance of GRIN lens and working distance.
Figure 9:
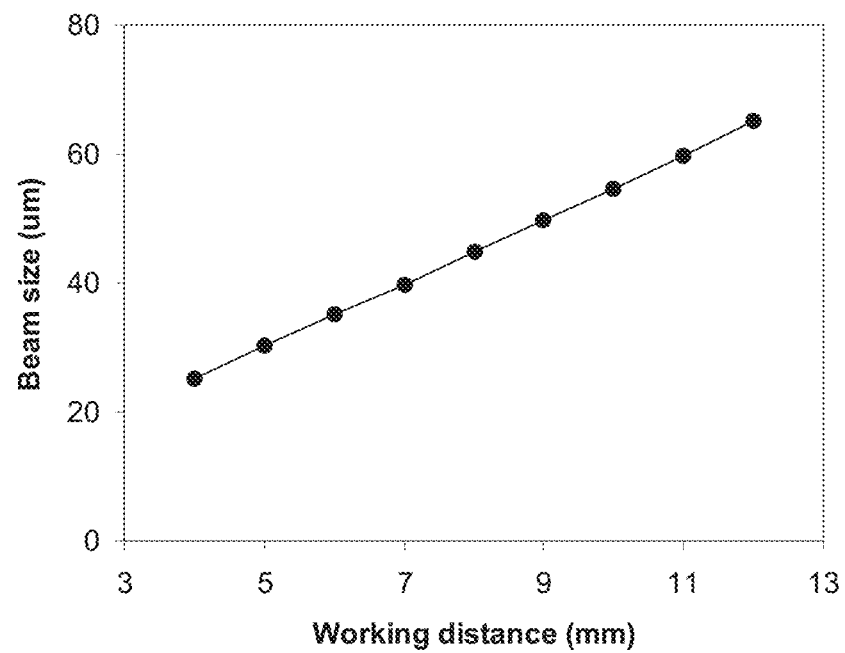
FIG. 9. Variation of focal size of probe beam at different working distance.

FIG. 8 shows the spot size of probe beam at the entrance of the GRIN lens at different working distances between 4 to 12 mm. The beam size is analyzed based on paraxial Gaussian beam propagation with Zemax. At working distance of 12 mm, the maximum beam spot size is about 0.26 mm. This is smaller than the 0.5 mm diameter of the employed GRIN lens. Thus, the OCT probe beam can transit through the GRIN lens safely. The focal spot size of probe beam in human retina is shown in FIG. 9, where the horizontal axis is working distance. The vertical axis shows the focal spot size, which ranges from 25.2 to 65.2 µm.

Example 3 Fundus Illumination

Figure 10:
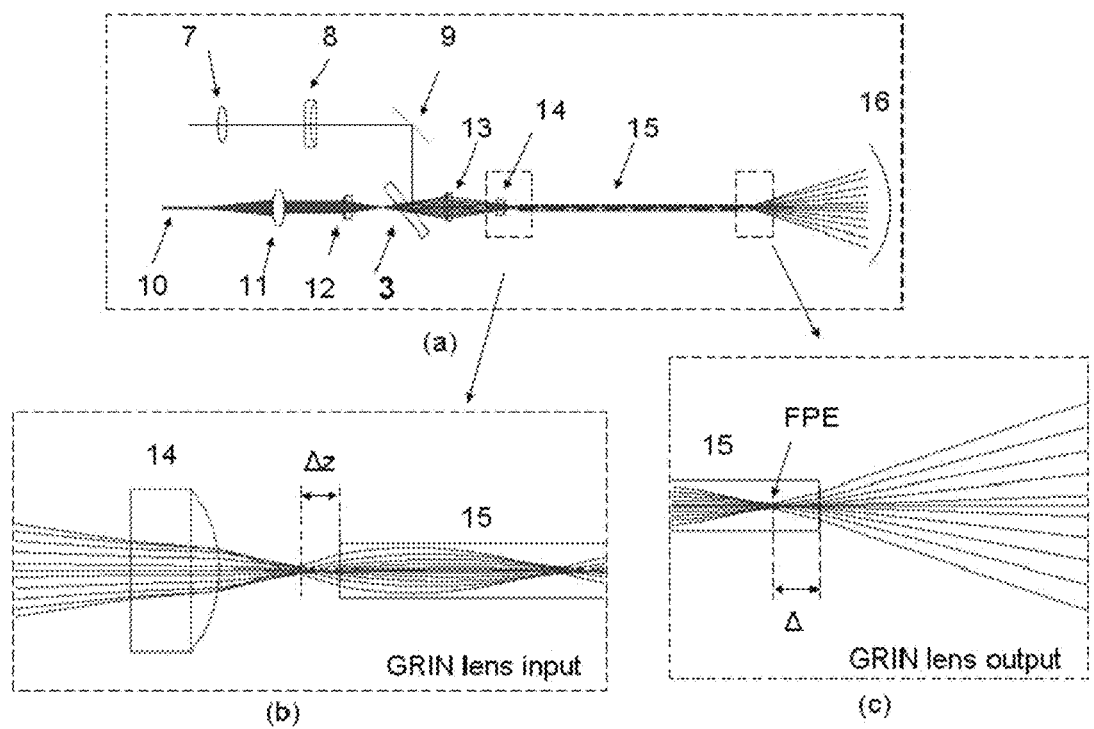
FIG. 10. Diagram of fundus illumination with Xenon arc lamp light.

Preferably, white light will be used for fundus illumination, so the operator can see the subject's retina through a microscope during surgery. Referring to FIG. 10 (*a*), light from Xenon arc lamp source travels through a multimode optical fiber 10 and enters probe. This light will be collimated by lens 11 and focused by lens 12. A focal point will be formed at the back focus position of lens 12. After light travelling through dichroic mirror 3, this focal point is relayed to the entrance of GRIN lens 15 by lens 13 and 14 to form a divergent beam in front of GRIN lens 15, as shown in FIG. 10 (*b*). There is a small displacement $\Delta z$ between the white light focal point and entrance surface of GRIN lens. After transmitting through GRIN lens, white light will illuminate human retina as an extended source. The illumination angle is about 37.40 based on Zemax simulation. The focal point of the extended source FPE will be inside the distal end of the GRIN lens with a displacement of $\Delta$, as shown in FIG. 10 (*c*). This small displacement can avoid ocular damage due to high light intensity induced by the small beam size inside the subject's eye.

Example 4—PZT Actuator Steering System

Figure 11:
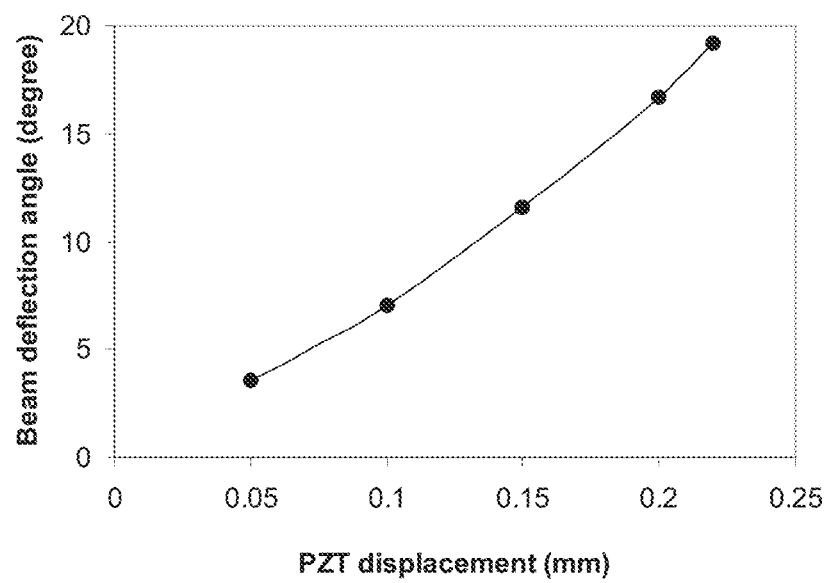
FIG. 11. Relationship between the probe beam deflection angle and the displacement of PZT bending.

Referring to FIG. 3, the sampling beam from swept source OCT system 5 is coupled into the probe P by single mode optical fiber 6 and collimated by lens 7. The collimated beam transmits through EWL lens 8 and reflected by mirror 33. Single mode fiber 6 is fixed onto a PZT actuator 32. The tip of single mode fiber 6 comprises a vertical or horizontal displacement while PZT bending with the applied voltage on it. This linear displacement is translated into an angular movement by lens 7 through its back focal point. The back focal point can be relayed onto the entrance surface of GRIN lens 15 by lens 34 and lens 37 such that probe beam can transmit through the GRIN lens during its angular movement. After passing through the four pitches GRIN lens 15, probe beam will scan the subject's retina through its angular movement. FIG. 11 shows the relationship between beam deflection angle and fiber tip displacement. A deflection angle of 190 can be achieved at a displacement of 0.22 mm. In this example, EWL lens 8 is set at the back focal position of lens 7 to supply beam focusing while not disturbing the OCT beam scan. By changing the curvature of the interface between two aqueous materials inside lens 8 electrically, its focal length can be adjusted to change the working distance between the distal end of the GRIN lens 15 and retina 16 effectively. Referring to FIG. 3, white light from Xenon arc lamp source 17 travels through a multimode optic fiber 10 and is collimated by lens 11. The collimated beam will be focused by lens 35 at first. The back focal point of lens 35 is relayed to the entrance of GRIN lens 15 by lens 36 and 37. This will form a divergent beam in front of GRIN lens 15. There is a small displacement between the white light focal point and entrance surface of GRIN lens 15, as shown in FIG. 10 (b). After traveling through GRIN lens 15, white light will illuminate human retina as an extended source with its focal point inside the GRIN lens, as shown in FIG. 10 (c).

Example 5—Scanning Pattern

Figure 12:
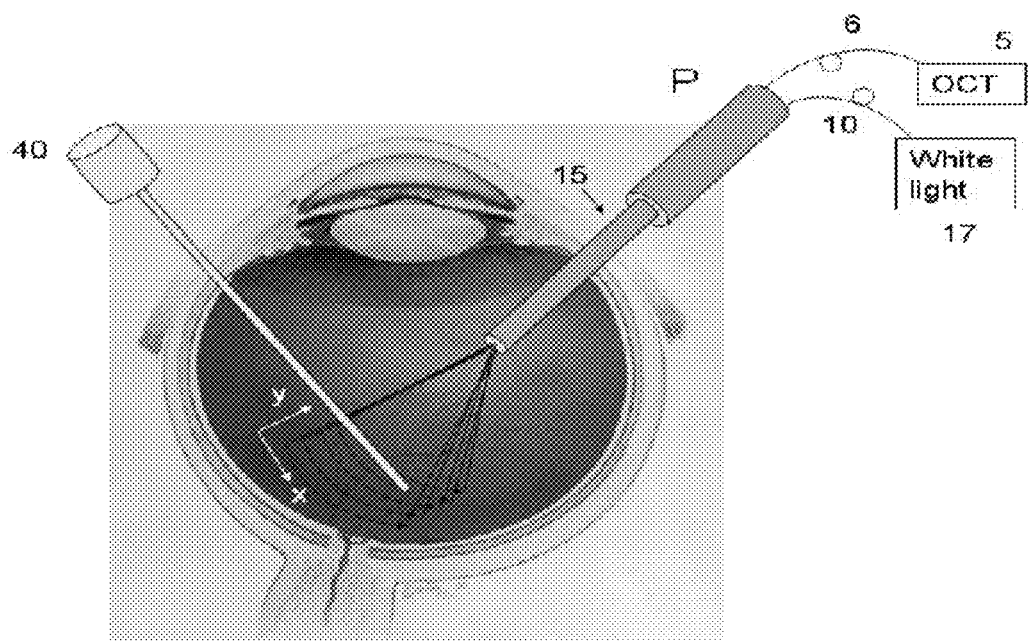
FIG. 12. Diagram of vitrectomy probe scanning pattern.

The angular movement of a probe beam induced by a MEMs mirror or PZT actuator can be translated to a linear movement on the human retina. FIG. 12 shows a diagram of desired 2D scanning pattern on the human retina. A tooth wave or sinusoidal wave voltage signal can be employed to drive the MEMs mirror or PZT actuator back and forth. The OCT probe beam from vitrecomy probe P provides a corresponding left and right motion on the retina surface in direction X to cover a desired scanning region (for example, 360 region). After finishing a one X dimensional scan, the probe beam can move back to its starting side with a small angle displacement, for example 2.90 degrees (or 0.5 mm), in the Y dimension for another X scan. In some examples, the OCT probe beam scans five or more different positions in the Y dimension to cover an 11.50 degree (or 2 mm) region. This scanning pattern will allows detection of the edge of the vitrectomy instrument 40 for retinal surgery.

Example 6—Volumetric Blood Flow Measurement

Retinal vein occlusions are the second leading cause of untreatable loss of vision in the elderly. Although there have been attempts to treat these occlusions surgically, these approaches have been mostly abandoned. A major barrier is the inability to measure blood vessel patency and flow during surgery and therefore an inability to measure a surgical endpoint.

Figure 13:
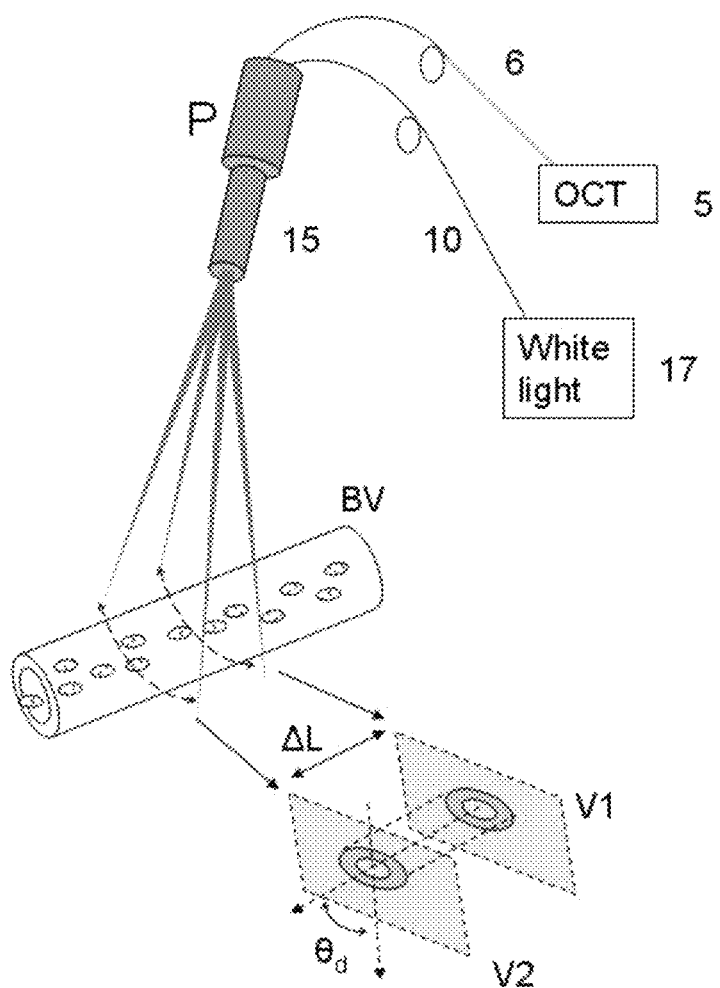
FIG. 13. Diagram of DSP method for blood flow measurement.

The disclosed vitrectomy probe allows the measurement of blood volume using the dual scanning plane (DSP) method described in Y. Wang et al, J Biomed Opt, 12, 041215-22 (2007); incorporated by reference herein). Referring to FIG. 13, using the DSP method, a probe beam from vitrectomy probe P will cross the same retinal blood vessel BV two times with a small displacement $\Delta L$. The position of the blood vessel in the two OCT images V1 and V2 will determine the relative position between scanning beam and flow direction. This will allow the user to determine the Doppler angle $\theta d$ between scanning beam and blood flow. With measured Doppler angle $\theta d$ and Doppler frequency shift, volume flow in the blood vessel can be determined. These will allow visualization of blood flow in retinal and choroidal vessels and can potentially guide treatments where the aims are either to open blocked vessels (retinal vein occlusion) or to close abnormal vessels.

Developmental and acquired retinal vascular disorders with high blood flow will leak serous fluid into and under the retina causing loss of vision. The approach to the management of advanced retinal hemangioblastomas and retinal telangiectasia often involves intraocular surgery to ablate the vascular anatomic abnormalities by either laser or freezing treatment after drainage of the subretinal fluid. This ablation is performed without a surgical endpoint and undertreatment is quite common. Intraocular OCT confirmation of complete ablation of the vascular abnormality with a vitrectomy probe would improve single surgery outcomes.

Example 7—Surgical Applications

This technology offers numerous features to guide the vitreoretinal surgeon during a variety of operations. This technology will be better able to define the anatomic differences between the internal limiting membrane (the basement membrane of the cells on the most anterior surface of the retina) and epiretinal membranes (pathologic membranes that often lie on top of the internal limiting membrane). The "peeling" of epiretinal membranes is a common vitreoretinal procedure that removes these pathologic membranes from the surface of the retina. The surgeon must be able to distinguish pathologic membrane from normal retina—the intraoperative OCT will better allow the surgeon to differentiate between pathologic and normal tissue Once an epiretinal membrane or the internal limiting membrane (which is often removed in macular hole surgery) has been removed, the OCT could be additionally be used as a very sensitive measure of whether removal was complete. Another use of this imaging modality will be to better define the planes of traction associated with pathologic proliferative membranes such as those seen with proliferative vitreoretinopathy and diabetic retinopathy, diseases which often result in blinding retinal detachments. In these conditions proliferative membranes become attached to the inner surface of the retina and contract in a way that separates the retina from the retinal pigment epithelium (a retinal detachment). Currently surgeons struggle to appreciate the various membranes involved, their points of retinal traction and surgeries are often complicated by the development of iatrogenic retinal breaks. An intraoperative OCT would permit the retinal surgeon to better understand the distribution of membranes, tractional forces and normal retina, and thereby increasing surgical safety. Additionally, intraoperative OCT could permit the assessment of subtle amounts of subretinal fluid that can be missed by current techniques.

Newer vitreoretinal surgical procedures require access into the subretinal space to deliver therapeutic agents (gene or stem cell therapy) or remove pathologic cells. Intraoperative OCT-guided cannulation of the subretinal space would be safer than the current approach as visualization of the narrow potential space between the photoreceptors and the retinal pigment epithelium would be improved. In addition, this approach would markedly improve the choice of retinotomy sites in the patients with pathologically thinned retinas (e.g. "dry" age-related macular degeneration and inherited retinopathies) as therapeutic agents should be injected at the transition areas between healthy (thicker) and unhealthy (thinner) retinal tissue. Drug delivery to a separate potential space, the suprachoroidal space, is also emerging as a therapeutically useful procedure. Transvitreal or periscleral access to this space is currently guided by visualization, "feel" and experience; real-time, OCT-guided visualization of the suprachoroidal space would result in safer access as catheter location could be accurately determined.

The invention claimed is:

1. A vitrectomy probe for insertion into tissue of a subject, comprising:
    a beam steering system for receiving a light beam from a sample arm optical fiber of an optical coherence tomography instrument and comprising
        a mirror, and
        an actuator coupled to the mirror that directs angular movement of a probe beam exiting the beam steering system in two dimensions;
    a fundus illumination system for receiving a beam of white light from a white light source via a multimode fiber;
    a light beam delivery system for illuminating a biological tissue of a subject with the probe beam from the beam steering system and illuminating the biological tissue of the subject with white illumination light from the fundus illumination system with an extended angle;
    a probe needle shaft small enough to fit through scleral incisions made for vitreoretinal surgery; and
    a dichroic mirror positioned to combine the probe beam and the white illumination light.

2. The vitrectomy probe of claim 1 wherein the beam steering system comprises a first collimating lens and an electrowetting lens.

3. The vitrectomy probe of claim 1 wherein the fundus illumination system comprises a first lens and a second lens, wherein the first lens is a collimating lens.

4. The vitrectomy probe of claim 1 wherein the beam delivery system comprises a first lens and a second lens, wherein the second lens is a GRIN lens and wherein the GRIN lens is configured to direct the probe beam to the eye of the subject and collect reflected light.

5. The vitrectomy probe of claim 4, wherein the GRIN lens has a length of at least 20 mm (4 pitches).

6. The vitrectomy probe of claim 4 wherein the GRIN lens has a diameter of 0.5 mm or less.

7. The vitrectomy probe of either claim 4 or claim 6, wherein the beam delivery system further comprises a third lens, and wherein the first lens and third lens are configured to relay a surface of a microelectromechanical system mirror to the entrance of the GRIN lens.

8. The vitrectomy probe of claim 1, wherein the biological tissue comprises a retina of the subject.

9. The vitrectomy probe of claim 1, wherein the dichroic mirror reflects the probe beam and transmits the white illumination light from the fundus illumination system.

* * * * *

UNITED STATES PATENT AND TRADEMARK OFFICE
CERTIFICATE OF CORRECTION

PATENT NO. : 10,070,784 B2
APPLICATION NO. : 14/890035
DATED : September 11, 2018
INVENTOR(S) : Huang et al.

Page 1 of 1

It is certified that error appears in the above-identified patent and that said Letters Patent is hereby corrected as shown below:

In the Specification

At Column 1, Line 8, please insert the following section indicating the governmental rights:
--GOVERNMENT SUPPORT
This invention was made with Government support under Grant Nos. R01 EY011289 and EY013516 awarded by the National Institutes of Health. The Government has certain rights in the invention.--

Signed and Sealed this
Twenty-fifth Day of June, 2019

Andrei Iancu
*Director of the United States Patent and Trademark Office*